United States Patent [19]
Miller et al.

[11] Patent Number: 6,069,158
[45] Date of Patent: May 30, 2000

[54] VITRONECTIN RECEPTOR ANTAGONISTS

[75] Inventors: William H. Miller, Schwenksville; William E. Bondinell, Wayne; Thomas Wen Fu Ku, Dresher, all of Pa.

[73] Assignee: SmithKline Beecham Corporation, Philadelphia, Pa.

[21] Appl. No.: 09/331,914

[22] PCT Filed: Jan. 8, 1998

[86] PCT No.: PCT/US98/00490

§ 371 Date: Jun. 29, 1999

§ 102(e) Date: Jun. 29, 1999

[87] PCT Pub. No.: WO98/30542

PCT Pub. Date: Jul. 16, 1998

Related U.S. Application Data

[60] Provisional application No. 60/034,026, Jan. 8, 1997.

[51] Int. Cl.$^7$ .......................... C07D 213/02; A61K 31/44
[52] U.S. Cl. .......................... 514/352; 546/312; 546/334; 514/357
[58] Field of Search ..................... 546/312.334; 514/352, 514/357

[56] References Cited

FOREIGN PATENT DOCUMENTS

WO 97/01540  1/1997  WIPO .

*Primary Examiner*—Zinna Northington Davis
*Attorney, Agent, or Firm*—Mary E. McCarthy; Stephne Venetianer; Charles M. Kinzig

[57] ABSTRACT

This invention relates to certain tricyclic compounds that are integrin receptor antagonists.

15 Claims, No Drawings

VITRONECTIN RECEPTOR ANTAGONISTS

This application is a 371 application of PCT/US98/00490 filed Jan. 8, 1998 which claims the benefit of priority to Provisional Application Ser. No. 60/034,026 filed Jan. 8, 1997.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembraiie glycoproteins expressed on a variety of cells. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et al., *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al., *J. Biol. Chem.*, 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.*, 1994, 28, 1815. Additionally, Brooks, et al., *Cell*, 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol.*, 1990, 71, 741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.*, 1993, 51, 206), and its role in angiogenesis has been confirmed. Brooks, et al., *Science*, 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 discloses that echistatin, a snake venom peptide which contains the RGD sequence, is a potent inhibitor of bone resorption in tissue culture, and inhibits attachment of osteoclasts to bone.

It has now been discovered that certain compounds are potent inhibitors of the $\alpha_v\beta_3$ and $\alpha_v\beta_5$ receptors. In particular, it has been discovered that such compounds are more potent inhibitors of the vitronectin receptor than the fibrinogen receptor.

SUMMARY OF THE INVENTION

This invention comprises compounds as described hereinafter, which have pharmacological activity for the inhibition of the vitronection receptor and are useful in the treatment of inflammation, cancer and cardiovascular disorders, such as atheroscleros is and restenosis, and diseases wherein bone resorption is a factor, such as osteoporosis.

This invention is also a pharmaceutical composition comprising compounds as described hereinafter and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. The novel compounds comprise a dibenzocycloheptene core in which a nitrogen-containing substituent is present on one of the aromatic six-membered rings of the dibenzocycloheptene and an aliphatic substituent containing an acidic moiety is present on the seven-membered ring of the dibenzocycloheptene. The dibenzocycloheptene ring system is believed to orient the substituent sidechains on the six and seven membered rings so that they may interact favorably with the vitronectin receptor. It is preferred that about twelve to fourteen intervening covalent bonds via the shortest intramolecular path will exist between the acidic group on the aliphatic substituent of the seven-membered ring of the dibenzocycloheptene and the nitrogen of the nitrogen-containing substituent on one of the aromatic six-membered ring of the dibenzocycloheptene.

Specific compounds of this invention are:

(±)-10,11-Dihydro-3-[3-(4-amino-2-pyridylamino)-1-propyloxy]-5H-dibenzo[a,d]cycloheptene-10-acetic acid;

(±)-10,11-Dihydro-3-[2-[6-(ethylamino)-2-pyridyl]-1-ethoxy]-5H-dibenzo[a,d]cycloheptene-10-acetic acid; and (±)-10,11-Dihydro-3-[3-(4-methyl-2-pyridylamino)-1-propyloxy]-5H-dibenzo[a,d]cycloheptene-10-acetic acid; or pharmaceutically acceptable salts thereof.

In cases wherein the compounds of this invention may have one or more chiral centers, unless specified, this invention includes each unique nonracemic compound which may be synthesized and resolved by conventional techniques.

Also included in this invention are prodrugs of the compounds of this invention. Prodrugs are considered to be any covalently bonded carriers which release the active parent drug (compounds of the instant invention) in vivo.

The compounds of this invention inhibit the binding of vitronectin and other RGD-containing peptides to the vitronectin receptor. Inhibition of the vitronectin receptor on osteoclasts inhibits osteoclastic bone resorption and is useful in the treatment of diseases wherein bone resorption is associated with pathology, such as osteoporosis and osteoarthritis.

In another aspect, this invention is a method for stimulating bone formation which comprises administering a compound which causes an increase in osteocalcin release. Increased bone production is a clear benefit in disease states wherein there is a deficiency of mineralized bone mass or remodeling of bone is desired, such as fracture healing and the prevention of bone fractures. Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behcet's disease, osteomalacia, hyperostosis and osteopetrosis, could benefit from administering a compound of this invention.

Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

The compounds of the present invention are also useful for the treatment, including prevention, of angiogenic disorders. The term angiogenic disorders as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

Another therapeutic target for the compounds of the instant invention are eye diseases chacterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of the present invention and an antineoplastic agent, such as topotecan and cisplatin.

This invention also provides for a process for preparing a compound of formula (I):

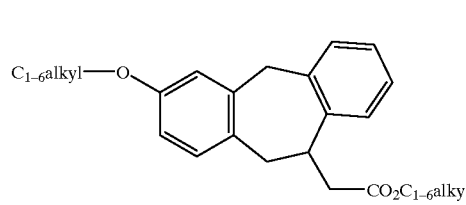

which process comprises reduction of a compound of formula (II):

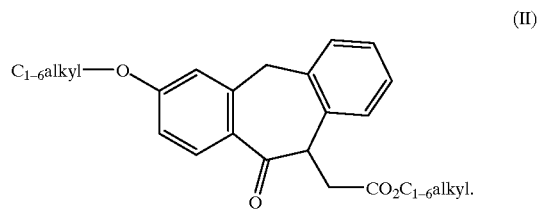

In another aspect of this invention is a process for preparing a compound of formula (II):

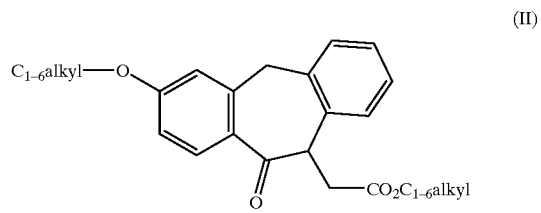

which process comprises cyclization of a compound of formula (III):

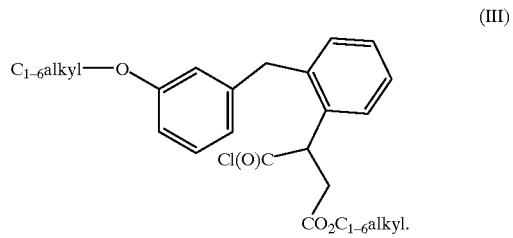

This invention further provides for novel intermediates of the formulae (IV), (V), (VI) and (II):

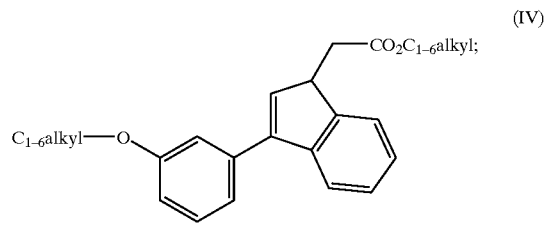

-continued

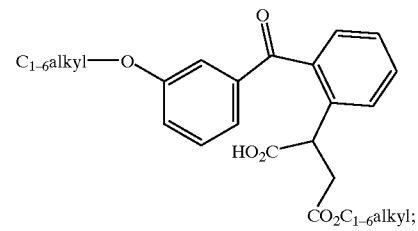

(V)

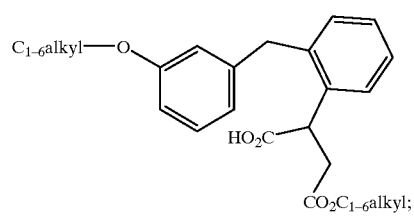

(VI)

and

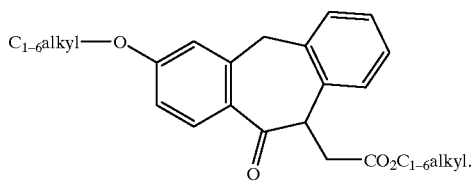

(II)

As used herein, C$_{1-6}$alkyl is meant to include methyl, ethyl, n-propyl, isopropyl, n-butyl, isobutyl, t-butyl, pentyl, n-pentyl, isopentyl, neopentyl and hexyl and the simple aliphatic isomers thereof.

Certain reagents are abbreviated herein. DCC refers to dicyclohexylcarbodiimide, DMAP refers to dimethylaminopyridine, DIEA refers to diisopropylethylamine, EDC refers to N-ethyl-N'(dimethylaminopropyl)-carbodiimide. HOBt refers to 1-hydroxybenzotriazole, THF refers to tetrahydrofuran, DMF refers to dimethyl formamide, NBS refers to N-bromo-succinimide, Pd/C refers to a palladium on carbon catalyst, DPPA refers to diphenylphosphoryl azide, BOP refers to benzotriazol-1-yloxy-tris(dimethylamino) phosphonium hexafluorophosphate, HF refers to hydrofluoric acid, PPA refers to polyphosphoric acid, TEA refers to triethylamine, TFA refers to trifluoroacetic acid, PCC refers to pyridinium chlorochromate.

Compounds of the instant invention are prepared by the methods described in Bondinell et al., PCT Publication No. WO 97/01540 (International Application No. PCT/US96/1 1108), published Jan. 16, 1997, the entire disclosure of which is incorporated herein by reference.

Additionally, compounds of this invention are prepared by methods analogous to those described in the schemes that are detailed hereinafter.

Scheme I

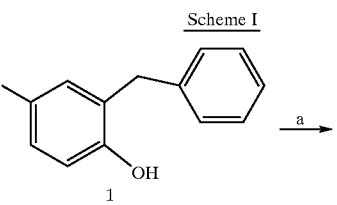
1

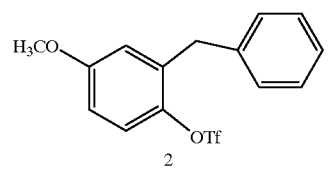
2

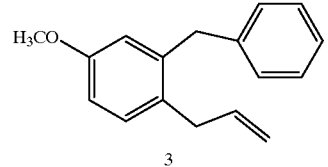
3

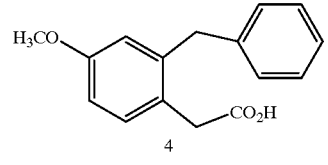
4

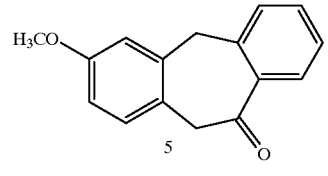
5

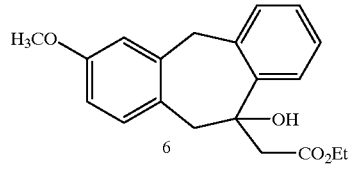
6

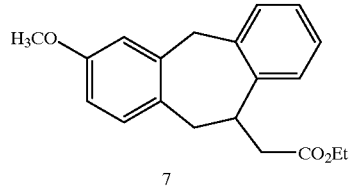
7

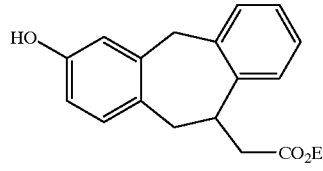
8

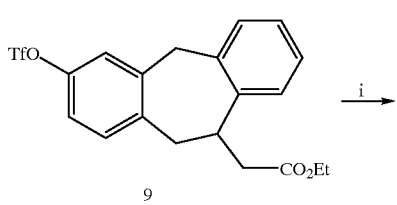
9

-continued

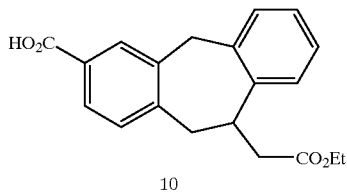
10 a) Tf₂O, 2,6-lutidine, CH₂Cl₂; b) allyltributyltin, LiCl, (Ph₃P)₂PdCl₂, DMF; c) RuCl₃, H₅IO₆, CCl₄, CH₃CN, H₂O; d) PPA; e) EtOAc/LiHMDS, THF; f) H₂, 10% Pd/C, conc. HCl, AcOH; g) EtSH, AlCl₃, CH₂Cl₂; h) Tf₂O, 2,6-lutidine, CH₂Cl₂; i) CO, Pd(OAc)₂, KOAc, dppf, DMSO.

2-Benzyl-4-metboxyphenol (*J. Am. Chem. Soc.* 1949, 71, 64) is converted to the corresponding trifluoromethanesulfonate ester, compound 2-Scheme 1(e.g., 1-2) by reaction with trifluoromethanesulfonic anhydride (Tf₂O) in the presence of a suitable base, 2-Benzyl-4-methoxyphenol (*J. Am. Chem. Soc.* 1949, 71, 64) is converted to the corresponding trifluoromethanesulfonate ester, compound 2-Scheme 1(e.g., 1-2) by reaction with trifluoromethanesulfonic anhydride (Tf₂O) in the presence of a suitable base, for instance 2,6-lutidine, in an inert solvent, generally CH₂Cl₂. Reaction of 1-2 with allyltributyltin in the presence of LiCl and a palladium catalyst, for example bis(triphenylphosphine)palladium (II) chloride ((Ph₃P)₂PdCl₂), in an inert solvent such as DMF, by the method described by Tilley (*J. Org. Chem.* 1990, 55, 906), affords 1-3. Oxidative cleavage of the olefin in 3-Scheme 1 to afford directly the carboxylic acid 1-4 can be accomplished by reaction with an appropriate oxidizing agent, classically KMnO₄, in a suitable aqueous solvent, such as aqueous acetone or aqueous acetic acid. Preferably, however, oxidative cleavage of the olefin in 1-3 to afford directly the carboxylic acid 1-4 is conducted according to the general method of Sharpless (*J. Org. Chem.* 1981, 46, 393,5; *J. Org. Chem.* 1985, 50, 1560, footnote 4), wherein RuO₄ is generated in situ by the reaction of RuCl₃ or RuO₂ with NaIO₄ or H₅IO₆ in a solvent mixture of CCl₄, CH₃CN, and H₂O. Alternatively, the oxidation might be conducted in two operations, involving in the first stage an oxidative cleavage of the olefin to the corresponding aldehyde, which can be accomplished by procedures well known to those of skill in the art, followed by oxidation of the aldehyde to the carboxylic acid using, for example, NaClO₂ as described by Pinnick (*Tetrahedron* 1981, 37, 2091) or by Dalcanale and Montanari (*J. Org. Chem.* 1986, 51, 567). Cyclization of 1-4 to 1-5 can be accomplished using polyphosphoric acid, according to the method described by Proctor, Renfrew, and Savage (*J. Chem. Soc.* (C) 1969, 1000). Alternatively, 1-4 can be converted to 1-5 via the corresponding acid chloride of 1-4, which can be prepared by methods well-known to those of skill in the art. Treatment of this acid chloride with an appropriate Friedel-Crafts catalyst, such as AlCl₃ or SnCl₄, in an inert solvent, such as CH₂Cl₂ or CS₂, provides the cyclic ketone 1-5. Reaction of 1-5 in an aldol-type reaction with the enolate of ethyl acetate, which can be generated from ethyl acetate on exposure to an appropriate amide base, for instance lithium diisopropylamide (LDA) or lithium bis(trimethylsilyl)amide (LiHMDS), gives 1-6. Frequently, THF is the solvent of choice for an aldol reaction, although THF in the presence of various additives, for instance HMPA or TMEDA, is often used. Reduction of 1-6 to give 1-7 can be accomplished by hydrogenolysis over an appropriate catalyst, for example palladium metal on activated carbon (Pd/C), in an appropriate solvent, such as acetic acid, in the presence of a mineral acid such as HCl. Alternatively, this reduction can be accomplished by treatment of 1-6 with triethylsilane in the presence of boron trifluoride etherate by the general method of Orphanopoulos and Smonu (*Synth. Commun.* 1988, 833). Removal of the methyl ether of 1-7 to give 1-8 can be accomplished with BBr₃ in an inert solvent, for example CH₂Cl₂, of by reaction with ethanethiol and AlCl₃ in an inert solvent, preferably CH₂Cl₂. Other useful methods for removal of a methyl ether are described in Greene, "Protective Groups in Organic Synthesis" (published by John Wiley and Sons). 1-9, the trifluoromethanesulfonate ester of 1-8, prepared by the method described earlier for the conversion of 1-1 to 1-2, reacts with carbon monoxide in the presence of potassium icetate, 1,1'-bis(diphenylphosphino)ferrocene (dppf), and a palladium catalyst, for instance palladium acetate (Pd(OAc)₂), in a suitable solvent, preferably DMSO, according to the general method described by Cacchi and Lupi (*Tet. Lett.* 1992, 33, 3939), to give 1-10.

Scheme 2 is illustrative of a carbon-oxygen bond forming coupling method that may be used to form an ether linkage.

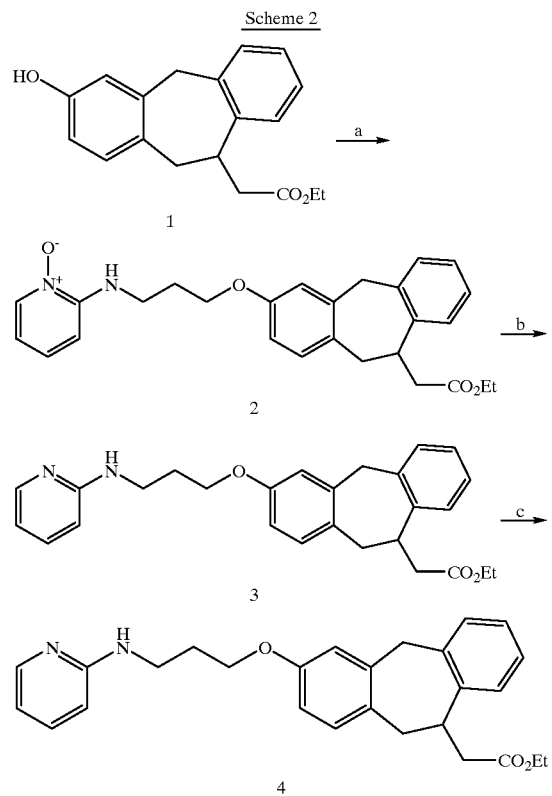

a) 2-[(3-hydroxy-1-propyl)amino]pyridine-N-oxide, DEAD, (Ph)₃P, DMF; b) cyclohexene, 10% Pd/C, 2-propanol; c) 1.0 N NaOH, EtOH, then acidification.

Compound 1 of Scheme 2 (2-1) is reacted with 2-[(3-hydroxy-1-propyl)amino]pyridine-N-oxide in a Mitsunobu-type coupling reaction (*Organic Reactions* 1992, 42, 335–656; *Synthesis* 1981, 1–28) to afford 2-2. The reaction is mediated by the complex formed between diethyl azodicarboxylate and triphenylphosphine, and is conducted in an aprotic solvent, for instance THF, CH₂Cl₂, or DMF. The pyridine-N-oxide moiety of 2-2 is reduced to the corresponding pyridine 2-3 under transfer hydrogenation conditions using a palladium catalyst, preferably palladium metal on activated carbon, in an inert solvent, for instance methanol, ethanol, or 2-propanol. Cyclohexene, 1,4-cyclohexadiene, formic acid, and salts of formic acid, such as potassium formate or ammonium formate, are commonly used as the hydrogen transfer reagent in this type of reaction. The ethyl ester of 2-3 is saponified as described in Scheme 1 to afford 2-4.

Alternate methods for preparing certain intermediate compounds described hereinbefore was accomplished as shown below in Schemes 3 and 4.

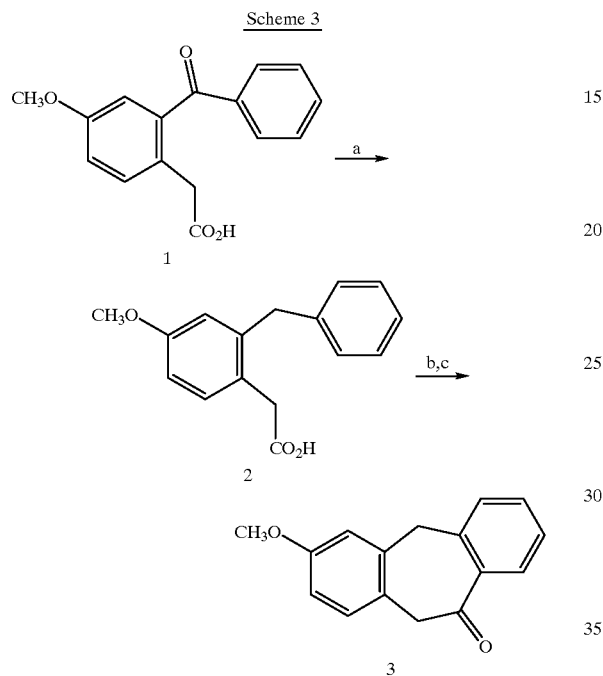

a) 10% Pd/C, HOAc; b) SOCl$_2$, toluene; c) AlCl$_3$, CH$_2$Cl$_2$

Scheme 3 summarizes an alternate method for preparing Scheme 1, formula 5 (1-5) compounds. According to this scheme, 3-1 (J. Med. Chem., 1981, 24, 998) is hydrogenated over an atmosphere of hydrogen gas at a suitable pressure, for example, 50 psi, in the presence of a palladium catalyst, for example, 10% Pd/C, in a suitable solvent, for example, glacial acetic acid, at a suitable temperature, for example, 25° C., to give 3-2. Cyclization of 3-2 to 3-3, is accomplished by first converting 3-2 to the corresponding acid chloride in the presence of a suitable chlorinating agent, for example, thionyl chloride, in a suitable solvent, for example, benzene, at a suitable temperature, for example, 85° C. Treatment of this acid chloride with a suitable Friedel-Crafts catalyst, for example, AlCl$_3$, in a suitable solvent, for example, CH$_2$Cl$_2$, at a suitable temperature, for example, 25° C., gives 6-3.

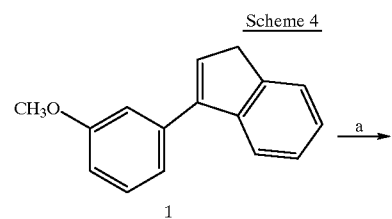

Scheme 4

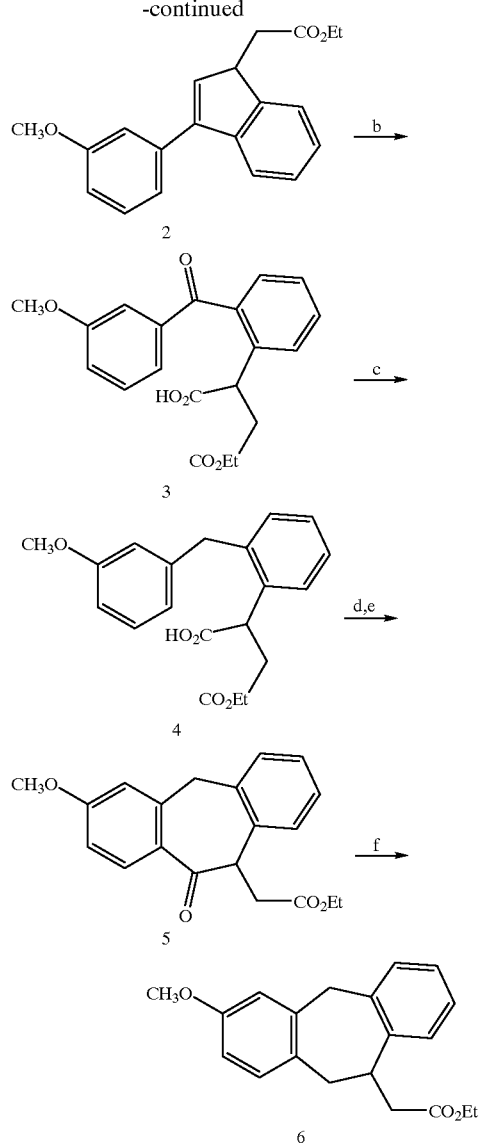

a) LiN(TMS)$_2$, ethyl bromoacetate; b) Jones reagent, OsO$_4$; c) H$_2$, 10% Pd/C, HOAC; d) C$_2$O$_2$Cl$_2$, DMF; e) AlCl$_3$, CH$_2$Cl$_2$, RT; f) H$_2$, 10% Pd/C, HOAC Scheme 4 summarizes an alternate method for preparing Scheme 1, formula 7 (1-7) compounds. According to this scheme, 4-1 (J. Med. Chem., 1981, 24, 998) is reacted with ethyl bromoacetate in the presence of a suitable base, for example, LiN(TMS)$_2$, in a suitable solvent, for example, THF, at a suitable temperature, for example, −78° C., to give 4-2. 4-2 is oxidatively cleaved in the presence of a suitable mixture of oxidants, for example, OsO$_4$/Jones reagent, in a suitable solvent, for example, acetone, at a suitable temperature, for example, 25° C., to give 4-3 (J. Org. Chem., 1993, 58, 4745). 4-3 is further hydrogenated over an atmosphere of hydrogen gas at a suitable pressure, for example, 50 psi, in the presence of a palladium catalyst, for example, 10% Pd/C, in a suitable solvent, for example, glacial acetic acid, at a suitable temperature, for example, 25° C., to give 4-4. Cyclization of 4-4 to 4-5, is accomplished by first converting 4-4 to the corresponding acid chloride in the presence of a suitable chlorinating agent, for example, oxalyl chloride, in the presence of catalytic amount of an additive, for example, DMF, in a suitable solvent, for example, $CH_2Cl_2$, at a suitable temperature, for example, 25° C. Treatment of this acid chloride with a suitable Friedel-Crafts catalyst, for example, $AlCl_3$, in a suitable solvent, for example, $CH_2Cl_2$, at a suitable temperature, for example, 25° C., gives 4-5. 4-5 is further hydrogenated over an atmosphere of hydrogen gas at a suitable pressure, for example, 50 psi, in the presence of a palladium catalyst, for example, 10% Pd/C, in a suitable solvent, for example, glacial acetic acid, at a suitable temperature, for example, 25° C., to give 4-6.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according as described herein and a pharmaceutically acceptable carrier. Accordingly, the compounds of this invention may be used in the manufacture of a medicament. Pharmaceutical compositions of the compounds of this invention prepared is hereinbefore described may be formulated as solutions or lyophilized powders for parenteral administration. Powders may be reconstituted by addition of a suitable diluent or other pharmaceutically acceptable carrier prior to use. The liquid formulation may be aL buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following; the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of osteoporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kglday. The precise level and method by which the compounds are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of this invention and other inhibitors of bone resorption, such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of this invention and an antineoplastic agent. Compounds of the camptothecin analog class, such as topotecan, irinotecan and 9-aminocamptothecin, and platinum coordination complexes, such as cisplatin, ormaplatin and tetraplatin, are well known groups of antineoplastic agents. Compounds of the camptothecin analog class are described in U.S. Pat. Nos. 5,004,758, 4,604,463, 4,473,692, 4,545,880 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med. Chem.*, 1980, 23, 554, Wani, et al., *J. Med. Chem.*, 1987, 30, 1774, and Nitta, et al., *Proc. 14th International Congr. Chemotherapy.*, 1985, *Anti-cancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S Pat. Nos. 5,562,925 and 4,310,515, the entire disclosure of each which is hereby incorporated by reference.

In the method of inhibiting tumor growth which comprises administering stepwise or in physical combination a compound of this invention and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter (mg/m$^2$) of body surface area per course of treatment. Infusions of the platinum coordination compound may be given one to two times weekly, and the weekly treatments may be repeated several times. Using a compound of the camptothecin analog class in a parenteral administration, the course of therapy generally employed is from about 0.1 to about 300.0 mg/m$^2$ of body surface area per day for about five consecutive days. Most preferably, the course of therapy employed for topotecan is from about 1.0 to about 2.0 mg/m$^2$ of body surface area per day for about five consecutive days. Preferably, the course of therapy is repeated at least once at about a seven day to about a twenty-eight day interval.

The pharmaceutical composition may be formulated with both the compound of this invention and the antineoplastic agent in the same container, but formulation in different containers is preferred. When both agents are provided in solution form, they can be contained in an infusion/injection system for simultaneous administration or in a tandem arrangement.

For convenient administration of the compound of this invention and the antineoplastic agent at the same or different times, a kit is prepared, comprising, in a single container, such as a box, carton or other container, individual bottles, bags, vials or other containers each having an effective amount of the compound of this invention for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of this invention may be in an i.v. injectable form, or infusion bag linked in series, via tubing, to the antineoplastic agent in a second infusion bag. Using such a system, a patient can receive an initial bolus-type injection or infusion of the compound of this invention followed by an infusion of the antineoplastic agent.

The compounds may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg|mL) in buffer T (containing 2 mM CaCl$_2$ and 1% octylglucoside) was diluted with buffer T containing 1 mM CaCl$_2$, 1 mM MnCl$_2$, 1 mM MgCl$_2$ (buffer A) and 0.05% NaN$_3$, and then immediately added to 96-well ELISA plates (Corning, New York, N.Y.) at 0.1 mL per well. 0.1–0.2 μg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM CaCl$_2$, 1 mM MnCl$_2$, 1 mM MgCl$_2$) to a final compound concentration of 100 μM. This solution is then diluted to the required final compound concentration. Various concentrations of unlabeled antagonists (0.001–100 μM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 μM SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to the equation: $K_i = IC_{50}/(1+L/K_d)$, where L and K$_d$ were the concentration and the dissociation constant of [$^3$H]-SK&F-107260, respectively.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of 2.5–5.0×10$^6$ cells/mL, and were pretreated with test compound at various concentrations for 20 min at 20° C. The solvent alone was used as control. 0.2 ml, of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% CO$_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rits, circulating ionized calcium levels are measured in whole blood immediately after it has been withdrawn by tail venipuncture into heparinized tubes. Rats are included if the ionized Ca level (measured with a Ciba-Coming model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1-34 peptide (HPTH 1-34, dose 1.25 ug/kg/h in saline/0.1% bovine serum albumin, Bachem, Ca) or a mixture of hPTH1-34 and test material, by continuous intravenous infusion via the venous catheter using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitve ELISA.

Assay 1 (using laser confocal microscopy)

Aliquots of human osteoclastoma-derived cell suspensions are removed from liquid nitrogen storage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 40° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 glitter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$ diluted to 100 ug/ml). The samples are incubated at 37° C. for 30 mins.

0.5 ml aliquots of the cells are seeded onto sterile dentine slices in a 48-well platte and incubated at 37° C. for 2 hours. Each treatment is screened in quadruplicate.

The slices are washed in six changes of warm PBS (10 ml / well in a 6-well plate) and then placed into fresh medium containing the compound treatment or control samples. The samples are incubated at 37° C. for 48 hours.

Tartrate Resistant Acid Phosphatase (TRAP) Procedure (selective stain for cells of the osteoclast lineage)

The bone slices containing the attached osteoclasts are washed in phosphate buffered saline and fixed in 2% gluteraldehyde (in 0.2M sodium cacodylate) for 5 min.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/ purple precipitate) are enumerated by bright-field microscopy and are then removed from the surface of the dentine by sonication.

Pit volumes are determined using the Nikon/Lasertec ILM21W confocal microscope.

Assay 2 (using an ELISA readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen storage, warmed rapidly at 37° C. and washed ×1 in RPMI-1640 medium by centrifugation (1000 rpm, 5 mins at 40° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method described above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tis;sue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His- Asp-Gly-Gly-Arg) that is present in the carboxy-terminal telopeptide of the a1-chain of type I collagen. The results are expressed as % inhibition of resorption compared to a vehicle control.

Human Osteoclast Adhesion Assay

The human osteoclasts are enriched and prepared for compound screening as described above in the initial 9 steps of Assay 1. For clarity, these steps are repeated hereinbelow.

Aliquots of human osteoclastoma-derived cell suspensions are removed from liquid nitrogen storage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5uglml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay

Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Streptomycin.

Constructs and Transfections

A 3.2 kb EcoRI-KpnI fragment of the $\alpha_v$ subunit and a 2.4 kb XbaI- XhoI fragment of the $\beta_3$ subunit were inserted into the EcoRI-EcoRV cloning sites of the pCDN vector (Aiyar et al., 1994 ) which contains a CMV promoter and a G418 selectable marker by blunt end ligation. For stable expression, $80 \times 10^6$ HEK 293 cells were electrotransformed with $\alpha_{v+\beta3}$ constructs (20 $\mu$g DNA of each subunit) using a Gene Pulser (Hensley et al., 1994 ) and plated in 100 mm plates ($5 \times 10^5$ cells/plate). After 48 hr, the growth medium was supplemented with 450 $\mu$g/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 $\mu$g/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0. 1% BSA at a density of $0.5 \times 10^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-Phase $\alpha_v\beta_5$ Binding Assay:

The vitronectin receptor $\alpha_v\beta_5$ was purified from human placenta. Receptor preparation was diluted with 50 mM Tris-HCl, pH 7.5, 100 mM NaCl, 1 mM CaCl$_2$, 1 mM MnCl$_2$, 1 mM MgCl$_2$ (buffer A) and was immediately added to 96-well ELISA plates at 0.1 ml per well. 0.1–0.2 µg of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer foi 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 µM) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion. The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 µM SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to Cheng and Prusoff equation: K$_i$=IC$_{50}$/(1+L/K$_d$), where L and K$_d$ were the concentration and the dissociation constant of [$^3$H]-SK&F-107260, respectively.

Inhibition of RGD-mediated GPIIb-IIIa binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 4° C. for 2 h. The lysate was centrifuged at 100,000 g for 1 h. The supermatant obtained was applied to a 5 mL lentil lectin sepharose 4B column (E.Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidyl choline (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dial,ysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 µg/mL polylysine (Sigma Chemical Co., St. Louis, Mo.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 pg of the purified platelet GPIIb-IIIa-containing liposomes. The mixtures were incubated for 1 h at room temperature. The GPIIb-IIIa-bound [$^3$H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 µM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist baseli on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis.

Preferred compounds of this invention have an affinity for the vitronectin receptor relative to the fibrinogen receptor of greater than 10:1. Most preferred compounds have a ratio of activity of greater than 100:1.

The efficacy of the compounds of this invention alone or in combination with an antineoplastic agent may be determined using several transplantable mouse tumor models. See U.S. Pat. Nos. 5,004,758 and 5,633,016 for details of these models The examples which follow are intended in no way to limit the scope of this invention, but are provided to illustrate how to make and use the compounds of this invention. Many other embodiments will be readily apparent to those skilled in the art.

EXAMPLES

General

Nuclear magnetic resonance spectra were recorded at either 250 or 400 MHz using, respectively, a Bruker AM 250 or Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5$\mu$ Apex-ODS indicates an octadecylsilyl derivatized silica gel chromatographic support having a nominal particle size of 5$\mu$, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of Ethyl (±)-10,11-dihydro-3-carboxy-5H-dibenzo[a.d]cycloheptene-10-acetate a) 3-Benzyl-4-(trifluoromethanesulfonyloxy)anisole Trifluoromethanesulfonic anhydride (10.0 mL, 60 mmol) was added over 3 min to a solution of 2-benzyl-4-methoxyphenol (10.71 g, 50 mmol; prepared according to *J. Am. Chem. Soc.* 1949, 71, 64) and anhydrous 2,6-lutidine (12.0 mL, 100 mmol) in anhydrous $CH_2C_2$ (250 mL) at −78° C. under argon. The reaction was stirred at −78° C. for 0.5 h, then was warmed to RT. After 1 h, the reaction was diluted with hexanes (250 mL) and washed sequentially with 1.0 N HCl (2×100 mL), 1.0 N NaOH (2×50 mL), $H_2O$ (100 mL) and brine (50 mL). Drying ($Na_2SO_4$), concentration, and silica gel chromatography (10% EtOAc/hexanes) gave the title compound as a light yellow solid (16.65 g, 96%): TLC $R_f$ 0.51 (10% EtOAc/hexanes); $^1$H NMR (250 MHz, $CDCl_3$) δ 7.10–7.40 (m, 6H), 6.77 (dd, J=9.0, 3.1 Hz, 1H), 6.66 (d, J=3.1 Hz, 1H), 4.03 (s, 2H), 3.73 (s, 3H); FTIR ($CCl_4$) 1492, 1423, 1405, 1249, 1216, 1161, 1144, 1039, 869 cm $^1$; MS (ES) m/e 369 $(M+Na)^+$, 364.0 $(M+NH_4)^+$, 347.0 $(M+H)^+$.

b) 4-Allyl-3-benzylanisole

LiCl (3.08 g, 72.8 mmol) in a roundbottom flask was flame-dried in high vacuum, and the system was allowed to cool to RT under argon. 3-Benzyl-4-(trifluoromethanesulfonyloxy)anisole (21.0 g, 60.6 mmol), bis(triphenylphosphine)palladium(II) chloride (2.13 g, 3.0 mmol), anhydrous DMF (150 mL), and allyltributyltin (22.6 mL, 72.8 mmol) were added, and the mixture was purged with argon through three evacuation/argon flush cycles. The mixture was heated in an oil bath preset at 95° C., affording a yellow, homogeneous solution. After 1.5 h, the dark mixture was concentrated on the rotavap (high vacuum), and the residue was reconcerntrated from xylenes. The resulting residue was taken up in $Et_2O$ (120 mL) and stirred briskly with 10% KF (120 mL) for 0.5 h. The layers were separated, and the aqueous layer was extracted with $Et_2O$ (2×120 mL). The combined organics were filtered through celite® to remove the insoluble solids, and the filtrate was washed sequentially with $H_2O$ (60 mL) and brine (60 mL). Drying ($MgSO_4$) and concentration left a cloudy, yellow oil. Chromatography (silica gel, 5% EtOAc/hexanes) gave the title compound as a light yellow oil (14.21 g, 98%): TLC $R_f$ (5% EtOAc/hexanes) 0.51; $^1$H NMR (250 MHz, $CDCl_3$) δ 7.03–7.31 (m, 6H), 6.74 (dd, J=8.3, 2.7 Hz, 1H), 6.66 (d, J=2.7 Hz, 1H), 5.79–5.98 (m, 1H), 4.89–5.07 (m, 2H), 3.97 (s, 2H), 3.75 (s, 3H), 3.21–3.33 (m, 2H); FTIR ($CCl_4$) 1610, 1496, 1256, 1046, 914 $cm^{-1}$; MS (ES) m/e 239.2 $(M+H)^+$.

c) 2-Benzyl-4-methoxyphenylacetic Acid

A solution of $H_5IO_6$ (23.83 g, 104.5 mmol) in $H_2O$ (56 mL) was added to a solution of 4-allyl-3-benzyianisole (5.30 g, 22.24 mmol) in $CCl_4$ (28 mL) and $CH_3CN$ (28 mL), and the well-stirred mixture was cooled thoroughly to 0° C. $RuCl_3$ (231 mg, 1.11 mmol) was added, and the reaction was stirred briskly at 0° C. for 4 h, then at RT for 45 min. The mixture was filtered through celite®, and the filter pad was washed with $CH_2Cl_2$ (120 mL) then with $H_2O$ (120 mL). The layers were separated and the aqueous layer was extracted with $CH_2Cl_2$ (3×120 mL). Drying ($Na_2SO_4$) and concentration left a brown oil. This was partitioned between $Et_2O$ (90 mL) and 0.25 N NaOH (90 mL), and the layers were separated. The $Et_2O$ layer was extracted with 0.25 N NaOH (2×10 mL), and the combined aqueous layers were acidified (pH 2) with conc. HCl. $CH_2Cl_2$ extraction, drying ($Na_2SO_4$), and concentration gave the title compound as a yellow oil which solidifieti to a yellow solid (4.19 g, 74%): $^1$H NMR (250 MHz, $CDCl_3$) 8 7.05–7.35 (m, 6H), 6.77 (dd, J=8.3, 2.7 Hz, 1H), 6.71 (d, J=2.7 Hz, 1H), 4.00 (s, 2H), 3.76 (s, 3H), 3.54 (s, 2H); FTIR ($CCl_4$) 2300–3500 (broad), 1710, 1611, 1502, 1496, 1285, 1257, 1045 $cm^{-1}$; MS (ES) m/e 279.0 $(M+Na)^+$, 274.0 $(M+NH_4)^+$, 257.0 $(M+H)^+$.

d) 3-Methoxy-5H-dibenzo[a,d]cycloheptene-10(11H)-one

Finely powdered 2-benzyl-4-methoxyphenylacetic acid (3.26 g, 12.72 mmol) was added to well-stirred polyphosphoric acid (165 g) at 100–110° C. After 15 min, the reaction was poured onto ice (330 g). $Et_2O$ (330 mL) was added, and the mixture was stirred briskly for 15 min. The layers were separated, and the aqueous layer was extracted with $Et_2O$ (330 mL). The combined organic layers were washed with 5% $NaHCO_3$ (2×80 mL) then with brine (80 mL), dried ($MgSO_4$), and concentrated. The residue was reconcentrated from toluene, then was chromatographed (silica gel, 20% EtOAc/hexarnes). The title compound was obtained as a yellow solid (1.44 g, 48%): TLC $R_f$ (20% EtOAc/hexanes) 0.46; $^1$H NMR (250 MHz, $CDCl_3$) δ 8.07–8.15 (m, IH), 7.39–7.49 (m, 1H), 7.25–7.48 (m, 2H), 7.19 (d, J=8.3 Hz, 1H), 6.86 (d, J=2.6 Hz, 1H), 6.71 (dd, J=8.3, 2.6 Hz, 1H), 4.21 (s, 2H), 4.11 (s, 2H), 3.77 (s, 3H); FTIR ($CCl_4$) 1680, 1501, 1282, 1270 $cm^{-1}$; MS (ES) m/e 261 (M+Na)+, 256.0 $(M+NH_4)^+$, 239.0 $(M+H)^+$.

e) Ethyl (±)-10,11-dihydro-10-hydroxy-3-methoxy-5H-dibenzo[a,d]cycloheptene-10-acetate Anhydrous EtOAc (0.58 mL, 6.6 mmol) was added dropwise to a solution of ithium bis(trimethylsilyl)amide (1.0 M in THF, 6 mL, 6 mmol) in dry THF (24 mL) in a lame-dried flask at −78° C. under argon. The yellow solution was stirred at −78° C. for 0.5 h, then a solution of 3-methoxy-5H-dibenzo[a,d]cycloheptene-10(11H)-one (715 mg, 3 mmol) in dry THF (3 mL) was added dropwise over 3 min. Additional dry THF (0.4 mL) was used in transfer. After 0.5 h at −78° C., the reaction was quenched with saturated $NH_4Cl$ (15 mL), warmed to RT, and extracted with EtOAc (2×30 mL). Drying ($MgSO_4$), concentration, and chromatography (silica gel, 10% EtOAc/hexanes (400 mL), then 20% EtOAc/hexanes) gave recovered 3-methoxy-5H-dibenzo[a,d]cycloheptene-10(11H)-one (305.4 mg, 43%) as a yellow solid, followed by the title compound as a light yellow oil (531.9 mg, 54%): TLC $R_f$ 0.37 (20% EtOAc/hexanes); 1H NMR (250 MHz, CDCl$_3$) δ 7.63 (d, J=7.7 Hz, 1H), 7.00–7.30 (m, 4H), 6.80 (d, J=2.6 Hz, 1H), 6.69 (dd, J=8.2, 2.6 Hz, 1H), 3.95–4.35 (m, 2H), 4.07 (s, 2H), 3.76 (s, 3H), 3.68 (s, 1H), 3.64 (d, J=14.2 Hz, 1H), 3.35 (d, J=14.2 Hz, 1H), 2.79 (d, J=16.0 Hz, 1H), 2.66 (d, J=16.0 Hz, 1H), 1.22 (t, J=7.2 Hz, 3H); FTIR (CCl$_4$) 3580 (sharp), 3509 (broad), 1735, 1715, 1503, 1261, 1198, 1156, 1044 cm$^{-1}$; MS (ES) m/e 675.2 (2M+Na)$^+$, 653.2 (2M+H)$^+$.

f) Ethyl (±)-10,11-dihydro-3-methoxy-5H-dibenzo[a,d]cycloheptene-10-acetate

10% Pd/C (242 mg, 0.23 mmol) was added to a solution of ethyl (±)-10,11-dihydro-10-hydroxy-3-methoxy-5H-dibenzo[a,d]cycloheptene-10-acetate (741.1 mg, 2.27 mmol) and conc. HCl (0.19 mL, 2.27 mmol) in glacial AcOH (23 mL), and the mixture was shaken on a Parr apparatus at RT under H$_2$ (50 psi). After 6 h, the reaction was filtered through celite®, and the filter pad was washed with EtOAc. The filtrate was concentrated, and the residue was reconcentrated from toluene. The resulting faintly yellow, oily residue was chromatographed (silica gel, 20% EtOAc/hexanes) to afford the title compound as a colorless oil (643.6 mg, 91%): TLC $R_f$ 0.57 (20% EtOAc/hexanes); $^1$H NMR (250 Hz, CDCl$_3$) δ 7.05–7.22 (m, 4H), 7.01 (d, J=8.2 Hz, 1H), 6.76 (d, J=2.7 Hz, 1H), 6.67 (dd, J=8.2, 2.7 Hz, 1H), 4.30 (d, J=15.0Hz, 1H), 4.11–4.25 (m, 2H), 3.85 (d, J=15.0 Hz, 1H),3.70–3.90 (m, 1H), 3.77 (s, 3H), 3.31 (dd, J=15.0,4.1 Hz, 1H), 2.93 (dd, J=15.0, 9.2 Hz, 1H), 2.64 (dd, J=15.6, 5.0Hz, 1H), 2.52 (dd, J=15.6, 9.3 Hz, 1H), 1.27 (t, J=7.1 Hz, 3H); FTIR (CCl$_4$) 1734, 1611, 1504, 1285,1263, 1155, 1044cm$^{-1}$;MS (ES) m/e 333.0 (M+Na)$^+$, 328.0 (M+NH$_4$)$^+$, 311.0 (M+H)$^+$, 265.0 (M+H-EtOH)$^+$.

g) Ethyl (±)-10,11-dihydro-3-hydroxy-5H-dibenzo[a,d]cycloheptene-10-acetate

Anhydrous AlCl$_3$ (1.38 g, 10.35 mmol) was added all at once to a solution of ethyl (±)-10,11-dihydro-3-methoxy-5H-dibenzo[a,d]cycloheptene-10-acetate (643.6 mg, 2.07 mmol) in anhydrous CH$_2$Cl$_2$ (21 mL) at 0° C. under argon. The yellow solution was warmed to RT and stirred for 3 h, then was cooled to 0° C. and quenched with cold 3 N HCl (10 mL). The layers were separated, and the aqueous layer was extracted with CH$_2$Cl$_2$. The combined organic layers were dried (MgSO$_4$) and concentrated. Silica gel chromatography (25% EtOAc/hexanes) gave the title compound as a nearly colorless oil (611.7 mg, 100%): TLC $R_f$ 0.26 (20% EtOAc/hexanes); $^1$H NMR (400 MHz, CDCl$_3$) δ 7.03–7.22 (m, 4H), 6.93 (d, J=8.1 Hz, 1H), 6.69 (d, J=2.6 Hz, 1H), 6.58 (dd, J=8.1, 2.6 Hz, 1H), 5.00 (s, 1H), 4.25 (d, J=14.9 Hz, IH), 4.11–4.25 (m, 2H), 3.73–3.88 (m, 1H), 3.79 (d, J=14.9 Hz, 1H), 3.28 (dd, J=15.0, 4.1 Hz, 1H), 2.91 (dd, J=15.0, 9.3 Hz, 1H), 2.65 (dd, J=15.6, 4.9 Hz, 1H), 2.53 (dd, J=15.6, 9.5 Hz, 1H), 1.27 (t, J=7.2 Hz, 3H), FTIR (CCl$_4$) 3611 (sharp), 3447 (broad), 1734, 1504, 1291, 1272, 1176, 1152 cm$^{-1}$; MS (ES) m/e 314.2 (M+NH$_4$)$^+$, 297.2 (M+H)$^+$.

h) Ethyl (±)-10,11-dihydro-3-(trifluoromethanesulfonyloxy)-5H-dibenzo[a,d]cycloheptene-10-acetate Trifluoromethanesulfonic anhydride (0.45 mL, 2.68 mmol) was added dropwise to a solution of ethyl (±)-10,11-dihydro-3-hydroxy-5H-dibenzo[a,d]cycloheptene-10-acetate (611.7 mg, 2.06 mmol) and 2,6-lutidine (0.48 mL, 4.12 mmol) in anhydrous CH$_2$Cl$_2$ (10.3 mL) at −78° C. under argon. After 0.5 h, the reaction was warmed to RT and stirred for 1 h. The yellow solution was diluted with Et$_2$O (50 mL) and washed sequentially with 1.0 N HCl (5 mL), 5% NaHCO$_3$ (5 mL), and brine (5 mL). Drying (MgSO$_4$), concentration, and silica gel chromatography (20% EtOAc/hexanes) gave the title compound as a colorless oil (808.9 mg, 92%): TLC $R_f$ (20% EtOAc/hexanes) 0.58; $^1$H NMR (250 MHz, CDCl$_3$) δ 6.98–7.30 (m, 7H), 4.35 (d, J=15.2 Hz, 1H), 4.19 (q, J=7.1 Hz, 2H), 3.91 (d, J=15.2 Hz, 1H), 3.78–3.95 (m, 1H), 3.37 (dd, J=15.2, 4.1 Hz, 1H), 3.02 (dd, J=15.2, 9.6 Hz, 1H),2.70 (dd, J=15.8, 4.8 Hz, 1H), 2.53 (dd, J=15.8, 9.6 Hz, 1H), 1.27 (t, J=7.1 Hz, 3H); FTIR (CCl$_4$) 1735, 1493, 1427, 1250, 1215, 1144,961,856 cm$^{-1}$; MS (ES) m/e 451.1 (M+Na)$^+$, 446.2 (M+NH$_4$)$^+$, 429.2 (M+H)$^+$.

i) Ethyl (±)-10,11-dihydro-3-carboxy-5H-dibenzo[a,d]cycloheptene-10-acetate

A mixture of ethyl (±)-10,11-dihydro-3-(trifluoromethanesulfonyioxy)-5H-dibenzo[a,d]cycloheptene-10-acetate (808.9 mg, 1.89 mmol), KOAc (742 mg, 7.56 mmol), Pd(OAc)$_2$ (21.2 mg, 0.095 mmol), 1,1'-bis(diphenylphosphino)ferrocene (210 mg, 0.38 mmol), and anhydrous DMSO (11 mL) was purged with carbon monoxide (three evacuation/CO flush cycles, followed by bubbling CO through the mixture for 5 min), then was stirred under a balloon of CO in an oil bath set at 70° C. After 3.5 h, the reaction was diluted with H$_2$O (11 mL), cooled to 0° C., and acidified with 1.0 N HCl (ca. 8 mL). CH$_2$Cl$_2$ extraction (3×30 mL), drying (Na$_2$SO$_4$), concentration, and reconcentration from toluene left a reddish-orange liquid (2–3 mL). Chromatography (silica gel, 3:2:0.1 EtOAc/toluene/AcOH; mixed fractions again with 1:1:0.1 EtOAc/toluene/AcOH) gave the title compound (581.9 mg, 95%) as a viscous, yellow oil which partially crystallized in high vacuum at 40° C: TLC $R_f$ (3:2:0.1 EtOAc/toluene/AcOH) 0.60; $^1$H NMR (250 MHz, CDCl$_3$) δ 7.95 (d, J=1.5 Hz, 1H), 7.87 (dd, J=7.8, 1.5 Hz, 1H), 7.00–7.35 (m, 5H), 4.40 (d, J=15.2 Hz, 1H), 4.19 (q, J=7.1 Hz, 2H), 3.97 (d, J=15.2 Hz, 1H), 3.82–4.00 (m, 1H), 3.43 (dd, J=15.3, 4.0 Hz, 1H), 3.07 (dd, J=15.3, 9.5 Hz, 1H), 2.69 (dd, J=15.8, 4.8 Hz, 1H), 2.53 (dd, J=15.8, 9.5 Hz, 1H), 1.28 (t, J=7.1 Hz, 3H); FTIR (CCl$_4$) 2357–337 (broad), 1735, 1692, 1280 cm$^{-1}$; MS (ES) m/e 342.2 (M+NH$_4$)$^+$, 325.2 (M+H)$^+$, 307.2 (M+H-H$_2$O)$^+$.

Preparation 2

Preparation of Ethyl 2-Carboxy-10,11-dihydro-5H-dibenzo[a,d]cycloheptenyl-10-acetate a) Methyl 2-Benzoyl-5-methoxyphenylacetate Methyl 3-methoxy-phenylacetate was treated with benzoyl chloride and aluminum chloride as described in J. Chem. Soc., Perkin Trans 1, 1991, 171 to give the title compound.

b) Methyl 2-Benzyl-5-methoxyphenylacetate

The compound of Preparation 2(a) is treated with sodium borohydride and trifluoroacetic acid in dichloromethane according to the general procedure of Synthesis 1978, 763, to give the title compound.

c) 2-Benzyl-5-methoxyphenylacetic Acid

The compound of Preparation 2(b) is treated with aqueous sodium hydroxide and methanol and stirred. The mixture is concentrated and treated with dilute hydrochloric acid to give the title compound.

d) 5,11-Dihydro-2-methoxy-10H-dibenzo[a,d]cyclohepten-10-one

The compound of Preparation 2(c) is added to a mixture of phosphoric acid and phosphorous pentoxide stirred and heated to 80° C. according to the general procedure of U.S. Pat. No. 3,567,730 to give the title compound.

e) 5,11-Dihydro-2-hydroxy-10H-dibenzo[a,d]cyclohepten-10-one

The compound of Preparation 2(d) is treated with ethanethiol and aluminum chloride according to the general procedure of Tetrahedron. Letters 1978, 5211 to give the title compound.

f) 5,11-Dihydro-2-(trifluoromethanesulfonyl)oxy-10H-dibenzo[a,d]cyclohepten-10-one The compound of Preparation 2(e) is treated with triflic anhydride according to the general procedure of *J. Chem. Soc., Chem. Commun.* 1987, 904 to give the title compound.

g) 5,11-Dihydro-2-methoxycarbonyl-10H-dibenzo[a,d]cyclohepten-10-one

The compound of Preparation 2(f) is treated with carbon monoxide, methanol, palladium acetate and 1,3-bis(diphenylphosphino)propare in dimethyl sulfoxide according to the general procedure of *J. Chem. Soc., Chem. Commun.* 1987, 904 to give the title compound.

h) 5,11-Dihydro-2-carboxy-10H-dibenzo[a,d]cyclohepten-10-one

The compound of Preparation 2(g) is stirred with dilute aqueous sodium hydroxide. The mixture is treated with dilute hydrochloric acid to give the title compound.

i) 5,11-Dihydro-2-tert-butoxycarbonyl-10H-dibenzo[a,d]cyclohepten-10-one

The compound of Preparation 2(h) is treated with N,N-dimethylformamide di-tert-butyl acetal according to the general procedure of *Synthesis* 1983, 2, 135 to give the title compound.

j) Ethyl 2-tert-Butoxycarbonyl-5H-dibenzo[a,d]cycloheptene-10-acetate

The compound of Preparation 2(i) is treated with zinc powder and ethyl bromoacetate according to the general procedure of *Org. Reactions* 1947, 1, 1 and *J. Am. Chem. Soc.* 1938, 60, 2947 to give the title compound.

k) Ethyl 2-Carboxy-5H-dibenzo[a,d]cycloheptene-10-acetate

The compound of Preparation 2(f) was treated with trifluoroacetic acid in dichloromethane and stirred. The mixture is concentrated to give the title compound.

Preparation 3

Preparation of 2-[(2-aminoethy)aminoa]pyridine dihydrochloride a) Mono-Boc-1,2-ethylenediamine A solution of di-tert-butyl dicarbonate (10.91 g, 50 mmole) in $CH_2Cl_2$ (50 mL) was added dropwise over 30 min to a briskly stirred solution of 1,2-ethylenediamine (33 mL, 500 mmole) in $CH_2Cl_2$ (250 mL) at 0° C. under argon, A precipitate separated during the addition. When the addition was complete, the reaction was warmed to RT, stirred for 1 hr, and concentrated on the rotavap. The residue was taken up in $H_2O$ (100 mL) and filtered to remove a small amount of insoluble material. The filtrate was extracted with $CH_2Cl_2$ (3×100 mL), and the combined organics were dried ($MgSO_4$) and concentrated to afford the title compound (6.00 g, 75%) as a cloudy liquid: $^1H$ NMR (250, $CDCl_3$) δ 4.75–5.00 (m, 1 H), 3.05–3.25 (m, 2 H), 2.65–2.85 (m, 2 H), 1.46 (s, 9 H), 112 (br, s, 2H), b) 2-[[2-(Boc-amino)ethyl]amino]pyridine-N-oxide A mixture of mono-Boc-1,2-ethylenediamine (5.83 g, 36.39 mmole), 2-chloropyridine-N-oxide hydrochloride (7.25 g, 43.67 mmole), $NaHCO_3$ (15.29 g, 182 mmole), and tert-amyl alcohol (36 mL) was heated at reflux. After 47 hr, the dark brown mixture was cooled, diluted with $CH_2Cl_2$ (100 mL), and suction filtered to remove insoluble materials. The filtrate was concentrated and reconcentrated from toluene. Silica gel chromatography (10% MeOHlCHCl$_3$) gave impure title compound (8.23 g, 89%) as a yellow solid which was used without further purification: TLC (10% MeOH/CHCl$_3$) R$_f$ 0.42; $^1H$ NMR (250, $CDCl_3$) δ 8.16 (dd, J=6.5, 1.3 Hz, 1 H), 7.05–7.30 (m, 2 H), 6.68 (br d, J=8.6 Hz, 1 H), 6.50–6.65 (m, 1 H), 5.70–5.95 (m, 1 H), 3.25–3.60 (m, 4 H), 1.44 (s, 9 H); MS (ES) m/e 254 (M+H)$^+$.

c) 2-[[2-(Boc-amino)ethyl]amino]pyridine

10% Pd/C (106.4 mg, 0.10 mmole) was added to a solution of 2-[[2-(Boc-amino)ethyl]amino]pyridine-N-oxide (126.7 mg, 0.5 mmole) and cyclohexene (0.25 mL, 0.25 mmole) in absolute EtOH (5 mL), and the mixture was heated to reflux. After 16 hr, the reaction was filtered through celite® and the filtrate was concentrated. The residue was combined with the residue obtained from a separate preparation (0.5 mmole scale), and the combined materials were purified by silica gel chromatography (5% MeOH/CHCl$_3$). The title compound (148.4 mg, 63% based on 1 mmole of 2-[[2-(Boc-amnino)ethyl]amino]pyridine-N-oxide) was obtained as a yellow oil: TLC (5% MeOH/CHCl$_3$) R$_f$ 0.43; $^1H$ NMR (400, $CDCl_3$) δ 8.05–8.12 (m, 1 H), 7.37–7.46 (m, 1H), 6.53–6.61 (m, 1 H), 6.41 (d, J=8.3 Hz, 1 H), 5.12 (br s, 1 H), 4.86 (br s, 1 H), 3.26–3.51 (m, 4 H), 1.44 (s, 9 H); MS (ES) m/e 238 (M+H)$^+$.

d) 2-[(2-Aminoethyl)amino]pyridine dihydrochloride

4 N HCl in dioxane (3.2 mL) was added in a stream to a solution of 2-[[2-(Boc-amino)ethyl]amino]pyridine (148.4 mg, 0.63 mmole) in anhydrous $CH_2Cl_2$ (3.2 mL) at 0° C., then the reaction was warmed to RT. After 2 hr, the mixture was suction filtered to collect the precipitated solid, which was washed with anhydrous $Et_2O$ and dried to afford the title compound (132.8 mg, quantitative) as a yellow solid: $^1H$ NMR (400, $CD_3OD$) δ 7.99–8.07 (m, 1 H), 7.92–7.98 (m, 1 H), 7.19 (d, J=9.1 Hz, 1 H), 6.98–7.04 (m, 1 H), 3.76 (t, J=6.2 Hz, 2 H), 3.27 (t, J=6.2 Hz, 2 H, partially obscured by residual solvent signal); MS (ES) m/e 138 (M+H)$^+$.

Preparation 4

Preparation of 2-[(3-hydroxy-1-propyl)amino]pyridine-N-oxide a) 2-[(3-Hydroxy-1-propyl)amino]pyridine-N-oxide A mixture of 2-chloropyridine-N-oxide (1 6.6 g, 0.1 mole), 3-amino-1-propanol (15.3 mL, 0.2 mole), $NaHCO_3$ (42 g, 0.5 mole), and tert-amyl alcohol (100 mL) was heated to reflux. After 21 hr, the reaction was cooled, diluted with $CH_2Cl_2$ (300 mnL), and suction filtered to remove insoluble materials. The filtrate was concentrated and reconcentrated from toluene to leave a yellow oil. Silica gel chromatography (20% MeOH/CHCl$_3$) gave the title compound (15.62 g, 93%) as a yellow solid: TLC (20% MeOH/CHCl$_3$) R$_f$ 0.48; $^1H$ NMR (250, $CDCl_3$) δ 8.07 (dd, J=6.6, 1.2 Hz, 1 H), 7.34 (br t, 1 H), 7.10–7.30 (m, 1 H), 6.64 (dd, J=8.5, 1.4 Hz, 1 H), 6.40–6.60 (m, 1 H), 4.49 (br s, 1 H), 3.65–3.90 (m, 2 H), 3.35–3.60 (m, 2 H), 1.75–2.00 (m, 2 H); MS (ES) m/e 169 (M+H)$^+$.

Preparation 5

Preparation of 2-[(3-hydroxy-1-propyly)amino]-4-nitropyridine-N-oxide a) 2-[(3-Hydroxy-1-propyl)amino]-4-nitropyridine-N-oxide According to the procedure of Preparation 12, except substituting 2-chloro-4-nitropyridine-N-oxide (see Jain, P. C.; Chatterjee, S. K.; Anand, N. *Indian Journal of Chemistry* 1966, 403) for the 2-chloropyridine-N-oxide hydrochloride, the title compound was prepared as an orange solid: MS (ES) m/e 214.2 (M+H)$^+$.

Preparation 6

Preparation of 2-[(3-hydroxy-1-propyl)amino]-4-methylpyridine-N-oxide a) 2-[(3-Hydroxy-1-propyl)amino]-4-methylpyridine-N-oxide According to the procedure of Preparation 12, except substituting 2-chloro-4-methylpyridine-N-oxide (see Brown, E. V. *J. Amer. Chem. Soc.* 1957, 79, 3565) for the 2-chloropyridine-N-oxide hydrochloride, the title compound was prepared as an off-white solid: MS (ES) m/e 183 (M+H)$^+$.

Preparation 7

Preparation of 2-(ethylamino)-6-pyridylethanol a) 2-(N-Boc-amino)-6-picoline To a stirred solution of 2-amino-6-picoline (4.33 g, 40 mmol), Et$_3$N (6.2 mL, 40 mmol) and CH$_2$Cl$_2$ (50 mL) at 0° C. was added di-tert-butyl dicarbonate (9.6 g, 44 mmol). After stirring at RT overnight, the reaction mixture was concentrated in vacuum, diluted with H$_2$O, and extracted with CH$_2$Cl$_2$ (2×50 mL). Drying (MgSO$_4$) and concentration gave the title compound as colorless oil: MS (ES) m/e 209 (M+H)$^+$.

b) 2-(N-Boc-N-ethylamino)-6-picoline

To a suspension of NaH (60% dispersion in mineral oil, 1.15 g, 29.5 mmol) i.l DMF (50 mL) at 0° C. was added a solution of 2-(N-Boc-amino)-6-picoline in DMF (30 mL). The reaction was stirred at 0° C. for 15 min; then ethyl iodide (4.6 g, 30 mmol) was added. The reaction mixture was stirred at RT overnight; then was concentrated in vacuum. The residue was diluted with H$_2$O and extracted with CH$_2$Cl$_2$ (3×50 mL). Drying (MgSO$_4$), concentration, and silica gel chromatography (20% EtOAc/hexane) gave the title compound as colorless oil: MS (ES) m/e 237 (M+H)$^+$.

c) Ethyl 2-(N-Boc-N-ethylamino)-6-pyridylacetate LDA (0.018 mol) was prepared in THF (30 mL), cooled to −78° C., and 2-(N-Boc-N-ethylamino)-6-picoline (3.5 g, 15 mmol) was added, forming a deep red solution. After 15 min, diethyl carbonate (2.2 mL, 17.9 mmol) was added, the burgundy-colored solution was stirred at −78° C. for an additional 15 min, then the reaction was quenched with saturated NH$_4$Cl. The mixture was warmed to RT and extracted with EtOAc(3×30 mL). The combined organic layers were washed with brine, dried (MgSO$_4$), and concentrated. Silica gel chromatography (10% EtOAc/hexane) gave the title compound as colorless oil: MS (ES) m/e 309 (M+H)$^+$.

d) Ethyl 2-(ethylamino)-6-pyridylacetate

A solution of ethyl 2-(N-Boc-N-ethylamino)-6-pyridylacetate (1.5 g, 4.87 mmo)l) and 4M HCl/dioxane (5 mL, 20 mol) was stirred at RT overnight, then was concentrated. Reconcentration from toluene gave the title compound as white solid: MS (ES) m/e 209 (M+H)$^+$.

e) 2-(Ethylamino)-6-pyridylethanol

To a mechanically stirred solution of LiAlH$_4$ in THF(1.0 M, 20 mL, 20.4 mmol) was added dropwise a solution of ethyl 2-(ethylamino)-6-pyridylacetate (1 g, 4.1 mmol) in THF (30 mL). After the addition was completed, the reaction mixture was heated to reflux. After 5 hr, the reaction was cooled to 0° C. and quenched with 10% NaOH solution. The solids were removed by filtration, and the filtrate was concentrated in vacuum. The residue was dissolved in CH$_2$Cl$_2$, and the solution was dried (MgSO$_4$) and concentrated. Reconcentration from toluene (3 x) gave the title compound as a colorless oil: MS (ES) 167 (M+H)$^+$.

Preparation 8

Preparation of 10.11-Dihydro-3-methoxy -5H-dibenzo[a,d]cyclohepten-10-one a) 2-Benzyl-4-methoxyphenylacetic acid A solution of 2-benzoyl-4-methoxyphenylacetic acid (13.0 g, 0.048 mol), prepared by the method of *J. Med. Chem.* 1981, 24, 998, in glacial acetic acid (600 mL) was treated under argon with 4.3 g. of 10% Pd/C and hydrogenated at 50 psi for 17 hours. The mixture was filtered using celite® and the filtrate was concentrated and reconcentrated from toluene and methylene chloride to give 14.2 of the title compound: $^1$H NMR (400 MHz, CDCl$_3$) δ 3.52 (s, 2H), 3.75 (s, 3H), 4.0 (s, 3H), 6.7 (m, 2H), 7.15 (m, 6H).

b) 10,11-Dihydro-3-methoxy-5H-dibenzo[a,d]cycohepten-10-one

A solution of 2-benzyl-4-methoxyphenylacetic acid (14.2 g, 0.055 m) in benzene (120 mL) and thionyl chloride (28 mL) was refluxed for 1 hour and concentrated . The acid chloride was dissolved in dry methylene chloride (40 mL), and the solution was added dropwise under argon to a solution of AlC$_3$ (14.7 g, 0.11 mol) in methylene chloride (600 mL). The reaction was stirred under an argon atmosphere for 2.5 hours at room temperature, then was quenched with ice-water (200 mL). The layers were separated, and the organic phase was washed sequentially with 10% NaOH solution, water, and dil. HCl. The resulting solution was diluted with ether (200 mL), dried over MgSO$_4$, and concentrated. The solid residue was triturated with ether/hexane (1:1) and 9.35 g of the title compound was collected by filtration: Mp 105–106° C.; $^1$H NMR (400 MHz, CDCl$_3$) δ 3.72 (s, 3H), 4.1 (s, 2H), 4.2 (s, 2H), 6.7 (d, 1H), 6.82 (s, 1H), 7.30 (m, 4H), 8.1 (d, 1H).

Preparation 9

Preparation of Ethyl (±)-10,11-dihydro-3-methoxy-5H-dibenzo[a,d]cycloheptene-10-acetate a) Ethyl (±) 3-(3-methoxyphenyl)indeneacetate To a cold solution of 3-(3-methoxyphenyl)indene (4 g, 18 mmol), prepared by the method of *J. Med. Chem.* 1981, 24, 998, in THF (15 mL) at 0° C. was added dropwise a solution of LiN(TMS)$_2$ (20 mL, 1 M in THF) over 5 min. The resulting solution was added dropwise to a solution of ethyl bromoacetate (3.34 g, 20 mmol) in THF (15 mL) at −78° C. over 30 min. After 2.5 h, the mixture was quenched with saturated ammonium chloride solution and the layers were separated. The organic layer was dried over MgSO$_4$ and concentrated to give the crude product which was purified by column chromatography (SiO/2–4% EtOAc/hexane) to give title compound (1.1 g): $^1$H NMR (400 MHz, CDCl$_3$) δ 1.30 (t, 3H), 2.50 (m, 1H), 2.85 (m, 1H), 3.85 (s, 3H), 4.0 (m, 1H), 4.20 (q, 2H), 6.6 (s, 1H), 6.9 (m, 1H), 7.2 (s, 1H), 7.35 (m, 6H).

b) Ethyl (±) 3-[(3-methoxybenzoyl)]phenylsuccinate

A solution of ethyl (±) 3-(3-methoxyphenyl)indeneacetate (1.1 g, 3.6 mmol) in acetone (30 mL) was treated with 4% aqueous solution of osmium tetroxide (0.5 mL) followed by a dropwise addition of 1.2 M Jones reagent (5 mL, 6 mmol) according to the literature procedure (*J. Org. Chem.* 1993, 58, 4745). After stirring overnight at room temperature, the dark reaction mixture was quenched with isopropanol (2.5 mL), followed by sodium bisulfite (0.9 g) and water (30 mL). The product was extracted with ethyl acetate, washed with brine, dried over MgSO$_4$, and concentrated to give a solid residue. Trituration with 1:1 ether/hexane gave 0.76 g of the title compound: $^1$H NMR (400 MHz, CDCl$_3$) δ 1.18 (t, 3H), 2.90 (m, 1H), 3.3 (m, 1H), 3.92 (s, 3H), 4.1 (q, 2H), 4.4 (d, 1H), 7.25 (m, 2H), 7.5 (m, 6H).

c) Ethyl (±) 3-[(3-methoxybenzyl)]phenylsuccinate

A mixture of ethyl (±) 3-[(3-methoxybenzoyl)]phenylsuccinate (0.76 g., 2.1 mmol) and 10% Pd/C (0.6 g) in glacial acetic acid (35 mL) was hydrogenated at 50 psi for 17 hours. The mixture was filtered using celite® and the filter pad was washed with acetic acid. The filtrate was concentrated and reconcentrated from toluene and methylene chloride to give 0.65 g of the title compound: 1H NMR (400 MHz, CDCl$_3$) δ 1.20 (t, 3H), 2.20 (m, 1H), 3.0 (m, 1H), 3.74 (s, 3H), 4.1 (q, 2H), 4.18 (q, 2H), 4.4 (d, 1H), 6.2 (m, 2H), 7.22 (m, 6H).

d) Ethyl (±)-10,11-dihydro-3-methoxy-11-oxo-5H-dibenzo[a,d]cycloheptene-10-acetate To a magnetically stirred solution of ethyl (±) 3-[(3-methoxybenzyl)]phenylsuccinate (0.65 g, 1.9 mmol) in dry methylene chloride (10 mL) were added DMF (0.2 mL) and oxalyl chloride (0.2 mL, 2.28 mmol). After 1.5 h, the solution was added dropwise to a suspension of aluminum chloride (0.6 g, 4.5 mmol) in dry methylene chloride (15 mL). The mixture was quenched after 2 h with ice water, the layers were separated, and the aqueous layer was extracted with methylene chloride. The combined organic layers were dried over MgSO$_4$ and concentrated. The residue was purified by column chromatography (SiO$_2$/2–4% EtOAc/hexane) to give title compound (0.3 g): $^1$H NMR (400 MHz, CDCl$_3$) δ 1.28 (t, 3H), 2.88 (m, 1H), 3.55 (m, 1H), 3.84 (s, 3H), 3.88 (d, 1H), 4.18 (q, 2H), 4.85 (d, 1H), 4.95 (m, 1H), 5.8 (m, 2H), 7.22 (m, 4H), 8.1 (s, 1H).

e) Ethyl (±)-10,11-dihydro-3-methoxy-5H-dibenzo[a,d]cycloheptene-10-acetate

A mixture of ethyl (±)-10,11-dihydro-3-methoxy-11-oxo-5H-dibenzo[a,d]cycloheptetie-10-acetate (0.3 g., 0.93 mmol) and 10% Pd/C (0.3 g) in glacial acetic acid (25 mL) was hydrogenated at 50 psi for 18 hours. The mixture was filtered using celitee and washed with acetic acid. The filtrate was concentrated and reconcentrated from toluene and methylene chloride to give 0.25 g of the title compound: $^1$H NMR (400 MHz, CDCl$_3$) δ 1.28 (t, 3H), 2.60 (m, 2H), 2.90 (m, 1H), 3.30 (m, 1H), 3.80 (s, 3H), 3.85 (d, 1H), 4.18 (q, 2H), 4.30 (d, 1H), 6.70 (m, 2H), 7.0 (d, 1H), 7.22 (m, 4H).

The following compounds illustrate methods for preparing the biologically active compounds of this invention from intermediate compounds such as described in the foregoing Preparations.

Example 1

Preparation of (±)-10,11-dihydro-3-[3-(2-pyridylamino)-1-propyloxy]-5H-dibenzo[a,d]cycloheptene-10-acetic acid a) Ethyl (±)-10,11-dihydro-3-[3-[2-(N-oxopyridyl)amino]-1-propyloxy]-5H-dibenzo[a,d]cycloheptene-10-acetate A solution of 2-[(3-hydroxy-1-propyl)amino]pyridine-N-oxide (1.94 g, 11.55 mmole) and diethyl azodicarboxylate (1.8 mL, 11.55 mmole) in anhydrous DMF (58 mL) was added dropwise over 10 min to a solution of ethyl (±)-10,11-dihydro-3-hydroxy-5H-dibenzo[a,d]cycloheptene-10-acetate (1.37 g, 4.62 mmole) and triphenylphosphine (3.27 g, 12.47 mmole) in anhydrous DMF (23 mL) at RT under argon. After 23.5 hr, the reaction was concentrated on the rotavap, and the residue was reconcentrated from xylenes to remove residual DMF. Silica gel chromatography (30% EtOAc/hexanes (0.5 L), then EtOAc (1 L), then 5% MeOH/CHCl$_3$) gave recovered ethyl (±)-10,11-dihydro-3-hydioxy-5H-dibenzo[a,d]cycloheptene-10-acetate (298.1 mg, 22%), then the title compound (1.54 g, 75%) as a yellow oil: $^1$H NMR (250 MHz, CDCl$_3$) δ 8.10 (dd, J=6.6, 1.3 Hz, 1 H), 6.85–7.30 (m, 7 H), 6.78 (d, J =2.6 Hz, 1 H), 6.68 (dd, J=8.2, 2.6 Hz, 1 H), 6.61 (dd, J=8.5, 1.6 Hz, 1 H), 6.45–6.57 (m, 1 H), 4.29 (d, J=15.1 Hz, 1 H), 4.10–4.25 (m, 2 H), 4.06 (t, J=5.7 Hz, 2 H), 3.84 (d, J=15.1 Hz, 1 H), 3.70–3.92 (m, 1 H), 3.49 (q, J=6.5 Hz, 2H), 3.30 (dd, J=15.0, 4.2 Hz, 1 H), 2.93 (dd, J=15.0, 9.3 Hz, 1 H), 2.65 (dd, J=15.6, 5.1) 1 H), 2.51 (dd, J=15.6, 9.4 Hz, 1 H), 2.05–2.25 (m, 2 H), 1.27 (t, J=7.1 Hz, 3 H); MS (ES) m/e 447 (M+H)$^+$.

b) Ethyl (±)-10,11-dihydro-3-[3-(2-pyridylamino)-1-propyloxy]-5H-dibenzo[a,d]cycloheptene-10-acetate A mixture of ethyl (±)-10,11-dihydro-3-[3-[2-(N-oxopyridyl)amino]-1-propyloxy]-5H-dibenzo[a,d]cycloheptene-10-acetate (1.54 g, 3.45 mmole), 10% Pd/C (0.73 g, 0.69 mmole), cyclohexene (7 mL, 6.9 mmole), and isopropanol (35 mL) was heated at reflux for 2 hr, then the catalyst was removed by filtration through celite®. Concentration left a yellow oil, which was resubmitted to the reaction conditions. After 17 hr, the reaction was worked up as before, and yellow residue was again submitted to the reaction conditions, using 1:1 EtOAc/isopropanol (35 mL) instead of isopropanol as solvent. The mixture was heated at reflux for 5 hr, Pd black (73 mg, 0.69 mmole) was added, and reflux was continued for another 18.5 hr. Work up as before followed by silica gel chromatography (1:1 EtOAc/hexanes) gave the title compound (0.94 g, 63%) as a light yellow oil: TLC R$_f$ (1:1 EtOAc/hexanes) 0.38; $^1$H NMR (400 MHz, CDCl$_3$) δ 8.02–8.11 (m, 1 H), 7.33–7.42 (m, 1 H), 7.02–7.20 (m, 4 H), 7.00 (d, J=8.2 Hz, 1 H), 6.77 (d, J=2.6 Hz, 1 H), 6.67 (dd, J=8.2, 2.6 Hz, 1 H), 6.50–6.60 (m, 1H), 6.39 (d, J =8.5 Hz, 1 H), 4.69 (br t, 1 H), 4.29 (d, J=15.0Hz, 1 H), 4.11–4.25 (m, 2 H), 4.05 (t, J =5.8 Hz, 2 H), 3.84 (d, J=15.0 Hz, 1 H), 3.75–3.90 (m, 1 H), 3.48 (app. q, 2 H), 3.30 (dd, J=15.0, 4.1 Hz, 1 H), 2.93 (dd, J=15.0, 9.2 Hz, 1 H), 2.64 (dd, J=15.6, 4.8 Hz, 1 H), 2.52 (dd, J=15.6, 9.5 Hz, 1 H), 2.02–2.15 (m, 2 H), 1.27 (t, J=7.2Hz, 3 H); MS (ES) m/e 431 (M+H)$^+$.

c) (±)-10,11-Dihydro-3-[3-(2-pyridylamino)-1-propyloxy]-5H-dibenzo[a,d]cycloheptene-10-acetic acid A mixture of ethyl (±)-10,11-dihydro-3-[3-(2-pyridylamino)-1-propyloxy]-5H-dibenzo[a,d]cycloheptene-10-acetate (0.94 g, 2.18 mmole) and 1.0 N NaOH (2.6 mL, 2.62 mmole) in absolute EtOH (19.2 mL) is warmed in an oil bath set at 50° C. After 28.5 hr, the reaction was concentrated on the rotavap and the residue was purified by ODS chromatography (1:1 MeOH/H$_2$O). Concentration left a cloudy, aqueous solution, which was made homogeneous by addition of a little 1.0 N NaOH. The pH was adjusted to 7 with 1.0 N HCl, and the solid precipitate was collected and washed with H$_2$O. The mother liquors were concentrated, and the residue treated similarly to afford a small second crop. The combined materials were dried in high vacuum at 40° C. to afford the title compound (0.70 g, 79%) as a nearly colorless solid: HPLC (Hamilton PRP-1®, 40% CH$_3$CN/H$_2$O containing 0.1% TFA) k'=1.2; $^1$H NMR (400 MHz, DMSO-d$_6$) δ 7.94 (d, J=4.4 Hz, 1 H), 7.32–7.41 (m, 1 H), 7.03–7.22 (m, 4 H), 6.97 (d, J=8.4 Hz, 1 H), 6.83 (d, J=2.4 Hz, 1 H), 6.60–6.74 (m, 2 H), 6.41–6.50 (m, 2 H), 4.20 (d, J=14.7 Hz, 1 H), 4.00 (t, J=6.2 Hz, 2 H), 3.88 (d, J=14.7 Hz, 1 H), 3.60–3.70 (m, 1 H), 3.26–3.40 (m, 2 H, partially obscured by residual solvent signal), 3.20 (dd, J=15.1, 4.3 Hz, 1 H), 2.83 (dd, J=15.1, 10.3 Hz, 1 H), 2.60 (dd, J=15.9, 5.3 Hz, 1 H), 2.50 (dd, 1 H, partially obscured by residual solvent signal), 1.88–2.00 (m, 2 H); MS (ES) m/e 403 (M+H)$^+$. Anal. Calcd for C$_{25}$H$_{26}$N$_2$O$_3$ . 0.25 H$_2$O: C, 73.78; H, 6.56; N, 6.88. Found: C, 73.85; H, 6.47;

Example 2

Preparation of (±)-10,11-dihydro-3-[3-(4-amino-2-pyridylamino)-1-propyloxy]-5H-dibenzo[a,d]cycloheptene-10-acetic acid a) Ethyl (±)-10,11-dihydro-3-[3-[2-(4-nitro-N-oxopyridyl)amino]-1-propyloxy]-5H-dibenzo[a,d]cycloheptene-10-acetate According to the procedure of Example 1(a), except substituting 2-[(3-hydroxy-1-propyl)amino]-4- nitropyridine-N-oxide for the 2-[(3-hydroxy-1-propyl) amino]pyridine-N-oxide, the title compound was obtained following silica gel chromatography (gradient: 2:1 EtOAc/hexanes, then EtOAc, then 5% MeOH in 1:1 EtOAc/CHCl$_3$): MS (ES) m/e 492 (M+H)$^+$.

b) Ethyl (±)-10,11-dihydro-3-[3-(4-amino-2-pyridylamino)-1-propyloxy]-5H-dibenzo[a,d]cycloheptene-10-acetate According to the procedure of Example 1(b), except substituting ethyl (±)-10,11-dihydro-3-[3-[2-(4-nitro-N-oxopyridyl)amino]-1-propyloxy]-5H-dibenzo[a,d] cycloheptene-10-acetate for the ethyl (±)-10,11-dihydro-3-[3-[2-(N-oxopyridyl)amino]-1-propyloxy]-5H-dibenzo[a,d] cycloheptene-10-acetate, the title compound was obtained following silica gel chromatography (20% MeOH/CHCl$_3$): MS (ES) m/e 446 (M+H)$^+$.

c) (±)-10,11-Dihydro-3-[3-(4-amino-2-pyridylamino)-1-propyloxy]-5H-dibenzo[a,d]cycloheptene-10-acetic acid 1.0 N LiOH (0.74 mL, 0.74 mmole) was added all at once to a solution of ethyl (±)-10,11-dihydro-3-[3-(4-amino-2-pyridylamino)-1-propyloxy]-5H-dibenzo[a,d]cycloheptene-10-acetate (216.3 mg, 0.49 mmole) in THF (2.5 mL) and H$_2$O (1.8 mL) at RT. The two-phase mixture was warmed for 1 hr in an oil bath set at 40° C., then absolute EtOH (ca. 1 mL) was added to combine the phases. The reaction was kept at 40° C. for 19.5 hr, then was concentrated, and the residue was dissolved in 1:1 CH$_3$CN/H$_2$O (5 mL). The solution was acidified with TFA (0.11 mL, 1.47 mmoles) and concentrated. ODS chromatography (40% CH$_3$CN/H$_2$O containing 0.1% TFA) followed by concentration to remove CH$_3$CN left an oily, aqueous solution, which was made homogeneous by addition of a little CH$_3$CN. The pH was adjusted to 7 with 1.0 N NaOH, and an oily semisolid precipitated. The mixture was concentrated to remove the CH$_3$CN, and the resulting solid was collected. This was dissolved in aqueous NaOH, and the pH was adjusted to 7. The solid was collected, washed with plenty of H$_2$O, and dried in high vacuum at 45° C. to afford the title compound (133.3 mg, 61%) as an off-white solid: HPLC (Hamilton PRP-®, 35% CH$_3$CN/H$_2$O containing 0.1% TFA) k'=3.0; 1 H NMR (400 MHz, DMSO-d$_6$) δ 7.48 (d, J=6.3 Hz, 1 H), 7.04–7.22 (m, 4 H), 6.95 (d, J=8.2 Hz, 1 H), 6.88–7.02 (m, 1 H), 6.82 (d, J=2.4 Hz, 1 H), 6.67 (dd, J=8.2, 2.4 Hz, 1 H), 6.27 (br s, 2 H), 5.95 (dd, 1 H), 5.65 (narrow d, 1 H), 4.18 (d, J =14.7 Hz, 1 H), 4.00 (t, J=6.1 Hz, 2 H), 3.88 (d, J=14.7 Hz, 1 H), 3.59–3.70 (m, 1 H), 3.13–3.30 (m, 3 H), 2.82 (dd, J=15.2, 10.0 Hz, 1 H), 2.46 (dd, J=15.8, 8.8 Hz, 1 H, partially obscured by residual solvent signal), 2.58 (dd, J=15.8, 5.2 Hz, 1 H), 1.86–2.01 (m, 2 H); MS (ES) m/e 418 (M+H)$^+$. Anal. Calcd for C$_{25}$H$_{27}$N$_3$O$_3$ . 1.67 H$_2$O: C, 67.09; H, 6.83; N, 9.39. Found: C, 66.99; H, 6.59; N, 9.34.

Example 3

Preparation of (±)-10,11-Dihydro-3-[3-(4-methyl-2-pyridylamino)-1-propyloxy]-5H-dibenzo[a,d] cycloheptene-10-acetic acid a) Ethyl (±)-10,11-dihydro-3-[3-[2-(4-methyl-N-oxopyridyl)amino]-1-propyloxy]-5 H-dibenzo[a,d] cycloheptene-10-acetate According to the procedure of Example 1(a), except substituting 2-[(3-hydroxy-1-propyl)amino]-4-methylpyridine-N-oxide for the 2-[(3-hydroxy-1-propyl) amino]pyridine-N-oxide, the title compound was obtained as a pale yellow oil following silica gel chromatography (gradient: 30 ,50 ,100% EtOAc in hexane, then 1–5% MeOH in CHCl$_3$): MS (ES) m/e 461.3 (M+H)$^+$.

b) Ethyl (±)-10,11-dihydro-3-[3-(4-methyl-2-pyridylamino)-1-propyloxy]-5H-dibenzo[a,d]cycloheptene-10-acetate According to the procedure of Example 1(b), except substituting ethyl (±)-10,11-dihydro-3-[3-[2-(4-methyl-N-oxopyridyl)amino]-1-propyloxy]-5H-dibenzo[a,d] cycloheptene-10-acetate for the ethyl (±)-10,11-dihydro-3-[3-[2-(N-oxopyridyl)amino]-1-propyloxy]-5H-dibenzo[a,d] cycloheptene-10-acetate, the title compound was obtained following silica gel chromatography (gradient: 30–50% EtOAc in hexane): MS (ES) mie 445.3(M+H)$^+$.

c) (±)-10,11-Dihydro-3-[3-(4-methyl-2-pyridylamino)-1-propyloxy]-5H-dibenzo[a,d]cycloheptene-10-acetic acid 1.0 N NaOH (0.144 mL, 0.144 mmole) was added to a solution of ethyl (±)-10,11-dihydro-3-[3-(4-methyl-2-pyridylamino)-1-propyloxy]-5H-dibenzo[a,d]cycloheptene-10-acetate (35 mg, 0.08 mmole) in EtOH(5 mL) at RT. The mixture was warmed overnight in an oil bath set at 32° C., then was concentrated. The residue was dissolved in H$_2$O (3 mL), and the solution was acidified with 20% TFA. ODS chromatography (5–10% CH$_3$CN/H$_2$O containing 0.1% TFA) followed by concentration and lyophilization gave the title compound as a white powder: MS (ES) m/e 417.3(M+H)$^+$. Anal. Calcd for C$_{26}$H$_2$N$_2$O$_3$ . 2.0 TFA . 1.0 H$_2$O: C, 54.38; H,4.87; N, 4.23. Found: C, 54.66; H, 6.4.53; N, 4.32.

Example 4

Preparation of (±)-10,11-dihydro-3-[2-[6-(ethylamino)-2-pyridyl]-1-ethoxy]-5H-dibenzo[a,d] cycloheptene-10-acetic acid a) Ethyl (±)-10,11-dihydro-3-[2-[6-(ethylamino)-2-pyridyl]-1-ethoxy]-5H-dibenzo[a,d]cycloheptene-10-acetate According to the procedure of example 1(a), except substituting 2-(ethylamino)-6-pyridylethanol for the 2-[(3-hydroxy-1-propyl)amino]pyridine-N-oxide, the title compound was obtained as colorless oil following silica gel chromatography (5% MeOH/CH$_2$Cl$_2$): MS (ES) 445 (M+H)$^+$.

b) (±)-10,11-Dihydro-3-[2-[6-(ethylamino)-2-pyridyl]-1-ethoxy]-5H-dibenzo[a,d]cycloheptene-10-acetic acid Ethyl (±)-10,11-dihydro-3-[2-[6-(ethylamino)-2-pyridyl]-1-ethoxy]-5H-dibenzo[a,d]cycloheptene-10-acetic acid (80 mg, 0.18 mmol) was dissolved in MeOH (3 mL), and 1.0 N NaOH (0.22 mL, 0.22 mmol) was added. The solution was stirred at RT overnight, then was concentrated in vacuum. The residue was dissolved in H$_2$O (3 mL), and the solution was acidified with 20% TFA. Chromatography on C-18 Bond Elute (30% CH$_3$CN/H$_2$O containing 0. 1% TFA) gave the title compound as a white solid: MS(ES) 417 (M+H)$^+$. Anal. Calcd for C$_{26}$H$_{28}$N$_2$O$_3$ . 1.3 OF$_3$CO$_2$H: C, 60.83; H, 5.23; N, 4.96. Found: C, 60.64; H, 5.26; N, 4.26.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound which is:

(±)-10,11-Dihydro-3-[3-(4-amino-2-pyridylamino)-1-propyloxy]-5H-dibenzo[a,d]cycloheptene-10-acetic acid;

(±)-10,11-Dihydro-3-[2-[6-(ethylamino)-2-pyridyl]-1-ethoxy]-5H-dibenzo[a,d]cycloheptene-10-acetic acid; or (±)-10,11-Dihydro-3-[3-(4-methyl-2-pyridylamino)-1-propyloxy]-5H-dibenzo[a,d]cycloheptene-10-acetic acid; or a pharmaceutically acceptable salt thereof.

2. A pharmaceutical composition comprising a compound according to claim 1 and a pharmaceutically acceptable carrier.

3. A pharmaceutical composition which comprises a compound according to claim 1, an antineoplastic agent and a pharmaceutically acceptable carrier.

4. The pharmaceutical composition according to claim 3 wherein the antineoplastic agent is topotecan.

5. The pharmaceutical composition according to claim 3 wherein the antineoplastic agent is cisplatin.

6. A method of treating a disease state in which antagonism of the $\alpha_v\beta_3$ receptor is indicated which comprises administering to a subject in need thereof a compound according to claim 1.

7. A method of treating a disease state in which antagonism of the $\alpha_v\beta_5$ receptor is indicated which comprises administering to a subject in need thereof a compound according to claim 1.

8. A method of treating osteoporosis which comprises administering to a subject in need thereof a compound according to claim 1.

9. A method for inhibiting angiogenesis which comprises administering to a subject in need thereof a compound according to claim 1.

10. A method for inhibiting tumor growth or tumor metastasis which comprises administering to a subject in need thereof a compound according to claim 1.

11. A method of treating atherosclerosis or restenosis which comprises administering to a subject in need thereof a compound according to claim 1.

12. A method of treating inflammation which comprises administering to a subject in need thereof a compound according to claim 1.

13. A method of inhibiting tumor growth which comprises administering stepwise or in physical combination a compound according to claim 1 and an antineoplstic agent.

14. The method according to claim 13 wherein the antineoplastic agent is topotecan.

15. The method according to claim 13 wherein the antineoplastic agent is cisplatin.

* * * * *